(12) United States Patent
Choi et al.

(10) Patent No.: US 7,618,370 B2
(45) Date of Patent: Nov. 17, 2009

(54) VENOUS-ARTERIAL DETECTOR AND PRESSURE INDICATOR

(75) Inventors: Jai Seung Choi, Seoul (KR); Kelvin Yu Chung Liang, Bellevue, WA (US); Shente Steven Hsu, St. Louis, MO (US); Eric Chi Kuo Lee, Bethlehem, PA (US)

(73) Assignee: Device Evolutions LLC, Princeton, NJ (US)

( * ) Notice: Subject to any disclaimer, the term of this patent is extended or adjusted under 35 U.S.C. 154(b) by 0 days.

(21) Appl. No.: 11/745,634

(22) Filed: May 8, 2007

(65) Prior Publication Data
US 2007/0265550 A1    Nov. 15, 2007

Related U.S. Application Data

(60) Provisional application No. 60/798,865, filed on May 9, 2006.

(51) Int. Cl.
*A61B 5/00* (2006.01)
*A61B 5/02* (2006.01)

(52) U.S. Cl. .................. 600/371; 600/487; 604/168.01; 604/900

(58) Field of Classification Search .................. 600/371, 600/487; 604/168.01, 900
See application file for complete search history.

(56) References Cited

U.S. PATENT DOCUMENTS

| | | | | |
|---|---|---|---|---|
| 3,730,168 A | * | 5/1973 | McWhorter | 600/561 |
| 5,454,374 A | * | 10/1995 | Omachi | 600/486 |
| 2002/0055680 A1 | * | 5/2002 | Miele et al. | 600/450 |
| 2007/0260130 A1 | * | 11/2007 | Chin | 600/323 |

OTHER PUBLICATIONS

Reeves, A., et al., "Recent Trends in Central Venous Catheter Placement: A Comparison of Interventional Radiology with Other Specialities," J. Vascular and Interventional Radiology 12:1211-1214 (2001).

Amesur, N., et al., "Central Venous Access," Internet. http://www.emedicine.com/radio/topic859.htm. Last updated May 23, 2008. Last visited Sep. 10, 2008.

Horattas, M. and K. Hale., "Venous Access Devices," Internet. http://www.emedicinehealth.com/Articles/22043-1.asp. Last updated 2008. Last visited Sep. 10, 2008.

Bagwell, C., et al., "Potentially Lethal Complications of Central Venous Access Procedures," J. Ped. Surg. 35; 5:709-713 (2000).

(Continued)

*Primary Examiner*—Patricia C Mallari
(74) *Attorney, Agent, or Firm*—PatentBest; Andrew McAleavey

(57) ABSTRACT

A venous-arterial detector is disclosed. The detector includes a first chamber in fluid communication with a needle, and an indicator chamber in selective fluid communication with the first chamber through a valve. The indicator chamber is pre-pressurized to a defined pressure that preferably exceeds typical venous pressure, and the valve retains that pressure within the indicator chamber. When the needle is inserted into a vessel, if the pressure in the vessel is greater than the defined pressure in the indicator chamber, blood will flow into the indicator chamber, indicating that the vessel is most likely to be an artery.

20 Claims, 7 Drawing Sheets

OTHER PUBLICATIONS

Rothschild, J., "Ultrasound Guidance of Central Vein Catheterization," Making Healthcare Safer: A Critical Analysis of Patient Safety Practices, Agency for Healthcare Research and Quality, Evidence Report/Technology Assessment No. 43, Rockville, MD: Jul. 20, 2001.

Nicholson, T., et al., "Managing Arterial Catheterization During Central Venous Access Procedures," Cardiovasc. Intervent. Radiol. 27: 21-25 (2004).

Abbas, M., et al., "Method of Closing an Iatrogenic Subclavian Arterial Puncture," Indian J. Surg. 66:356-358 (2004).

Oliver, W.C., et al., "The Incidence of Artery Puncture with Central Venous Cannulation Using a Modified Technique for Detection and Prevention of Arterial Cannulation," J. Cardiothorac. Vasc. Anesth. 11(7):851-855 (Dec. 1997).

Anaesthesiauk, "Oxygen Content of Blood," Internet. http://www.frca.co.uk/article.aspx?articleid=100344. Last visited Sep. 10, 2008.

"Quick Reference Guide: Central Venous Lines," Nursing Standard 13(42) (Jul. 1999).

Jobes, D.R., et al., "Safer Jugular Vein Cannulation: Recognition of Arterial Puncture and Preferential Use of the External Jugular Route," Anesthesiology 59:353-355(1983).

Calvert, N., "The Effectiveness and Cost-Effectiveness of Ultrasound Locating Devices for Central Venous Access: A Systematic Review and Economic Evaluation," Health Technology Assessment 7(12): 30-32 (2003).

* cited by examiner

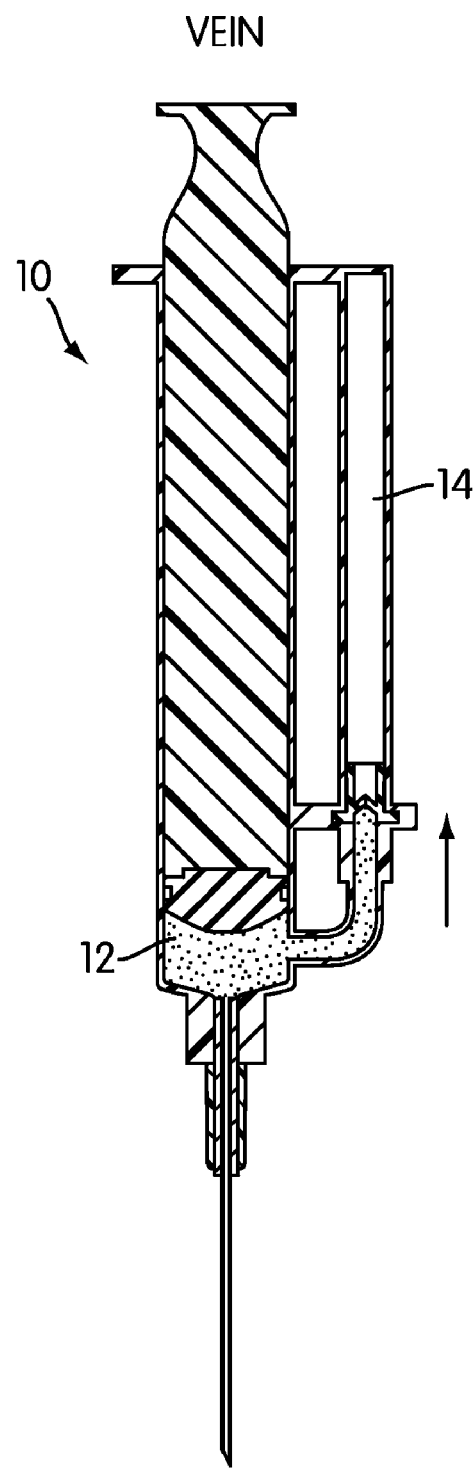
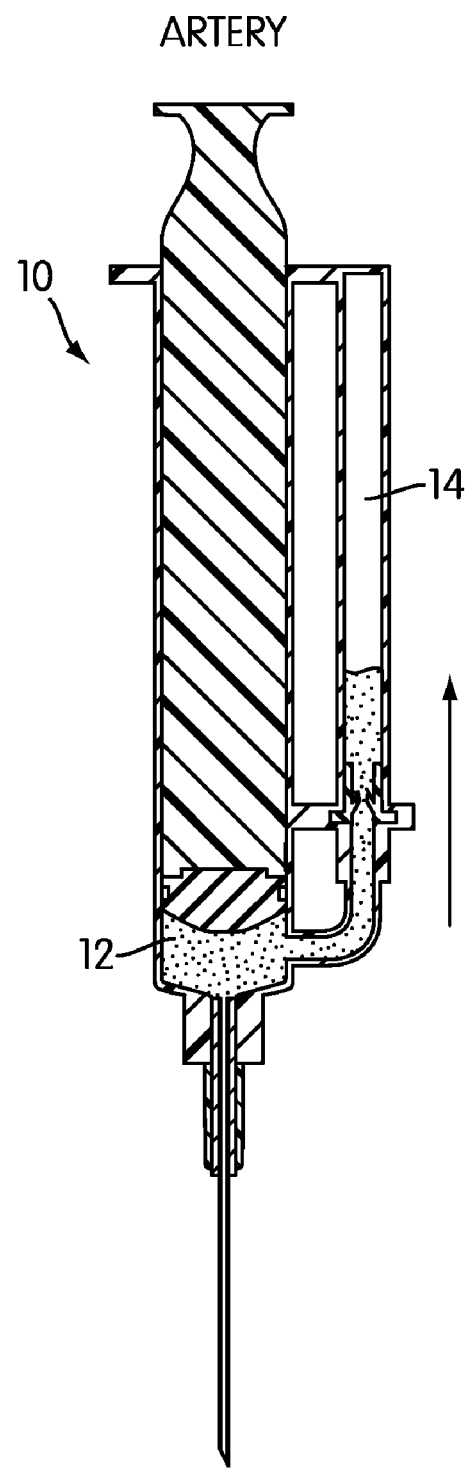
FIG. 5A  
FIG. 5B

VENOUS-ARTERIAL DETECTOR AND PRESSURE INDICATOR

CROSS-REFERENCE TO RELATED APPLICATIONS

This application claims priority to U.S. Provisional Patent Application No. 60/798,865, filed on May 9, 2006. That application is incorporated by reference in its entirety.

BACKGROUND OF THE INVENTION

1. Field of the Invention

In general, the invention relates to medical devices and, more specifically, to medical devices for blood vessel access.

2. Description of Related Art

The human vascular system includes three major types of blood vessels: arteries, muscular, relatively high-pressure vessels that carry blood away from the heart and toward the organs and tissues; veins, lower pressure vessels that return blood from the organs and tissues to the heart; and capillaries, the network of small vessels that distribute blood within the organs and tissues and connect the arteries with the veins.

During the course of medical treatment, it is often necessary to access the vascular system, for example, to deliver drugs or treatments, to take blood samples, and to gather information about the patient's vascular pressures and other aspects of their condition. Many procedures require access through a vein; other procedures require access through an artery. Generally, a hollow needle with either a syringe or a catheter attached is inserted into an artery or vein in order to obtain access.

However, it may be difficult for a clinician to determine whether he or she has punctured an artery or a vein. Differentiating between the two can be critical, for several reasons. For one, because arteries are typically at higher pressure than veins, inadvertently puncturing an artery can cause a great deal of bleeding. Aside from the immediate concern of bleeding, delivering a treatment designed for a vein into an artery can have serious adverse consequences for the patient.

Because of the importance of determining whether an artery or a vein has been entered, some techniques have evolved to differentiate between the two. For example, a physician seeking to place a central line in a patient might seek out, for example, the internal jugular vein by using a needle attached to an ordinary syringe. As the needle enters an artery or vein, the syringe fills with blood. Typically, the surgeon then tries to ascertain whether the vessel in question is an artery or vein by observing such things as the color of the blood (bright red oxygenated blood typically indicates an artery), the presence of a strong, pulsatile flow to the blood (also indicative of an artery), and the rate at which the syringe fills with blood (faster filling generally indicates an artery).

However, those observational techniques for differentiating between artery and vein are sometimes unreliable—for example, some patients may have an elevated venous pressure, and other patients, like hypovolemic patients, may have a deceptively low arterial pressure. In order to obtain a more definitive answer, the physician could, for example, disconnect the syringe from the needle and attach a pressure transducer, or could send the blood to a laboratory for a blood gas analysis, among other techniques. However, those techniques take more time, require more equipment, and may not be practical in emergency situations.

SUMMARY OF THE INVENTION

One aspect of the invention relates to venous-arterial detector. The detector comprises a first chamber, a needle, an indicator chamber, and a valve. The first chamber has a first opening at a first end and a second opening in a wall thereof. The needle is connected to and in fluid communication with the first chamber through the first opening. The indicator chamber is pre-pressurized to a defined pressure and is connected to the first chamber through the second opening in the first chamber. The valve is interposed between the first chamber and the indicator chamber so as to place the indicator chamber in selective fluid communication with the first chamber. The valve is constructed and arranged such that the defined pressure within the indicator chamber cannot pass through the valve, and thus remains within the indicator chamber; and fluid flowing from the first chamber toward the indicator chamber is permitted to pass through the valve. Blood entering the first chamber through the needle flows into the indicator chamber if the pressure of the blood is greater than the defined pressure within the indicator chamber.

Other aspects, features, and advantages of the invention will be set forth in the description that follows.

BRIEF DESCRIPTION OF THE DRAWINGS

The invention will be described with respect to the following drawing figures, in which like numerals represent like features throughout the figures, and in which:

FIGS. 5A and 5B are cross-sectional views of the venous-arterial detector of FIG. 1, illustrating the response of the detector to arterial puncture and venipuncture;

DETAILED DESCRIPTION

Figure 1:
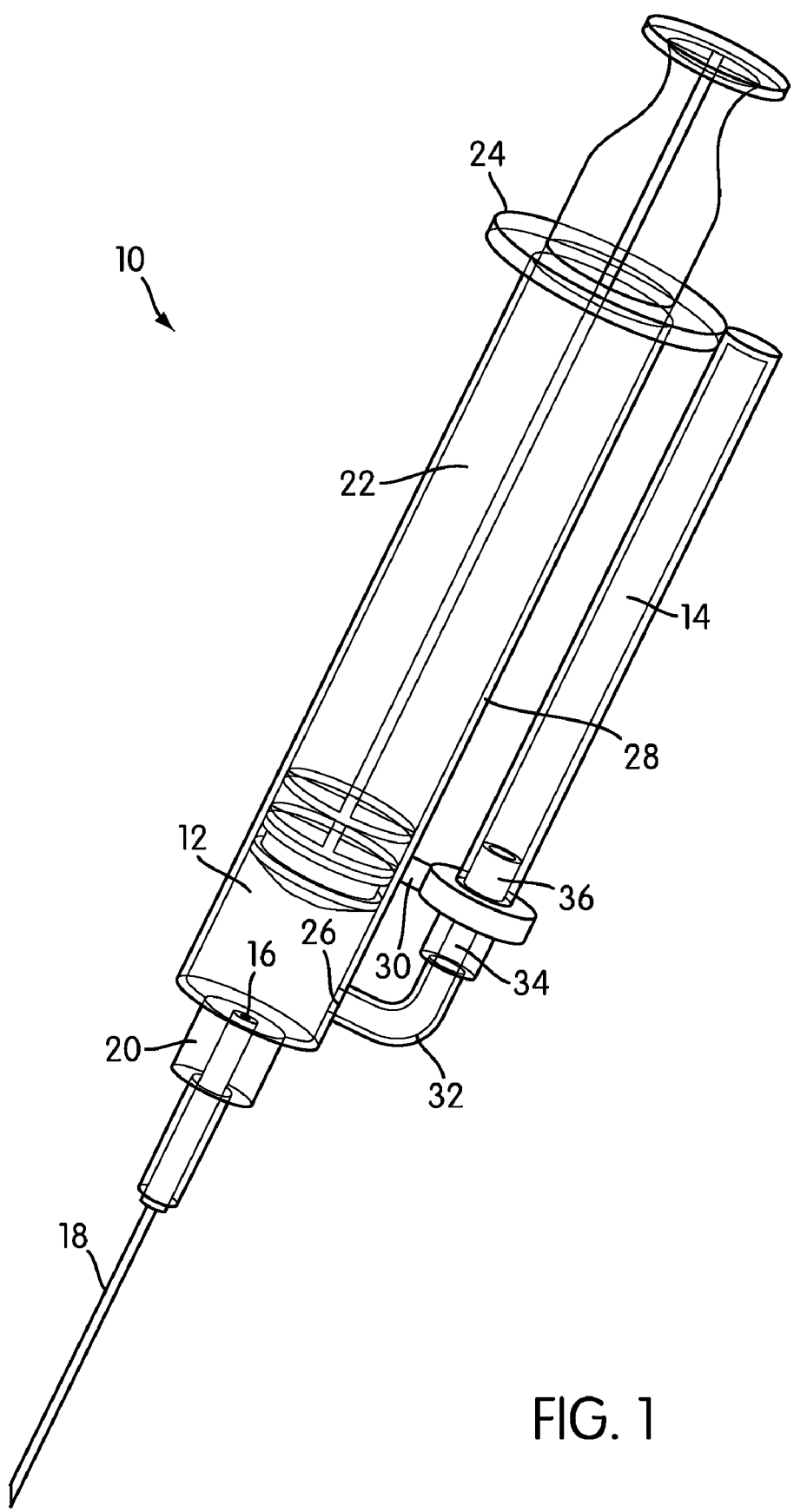
FIG. 1 is a perspective view of a venous-arterial detector according to one embodiment of the present invention.
Figure 2:
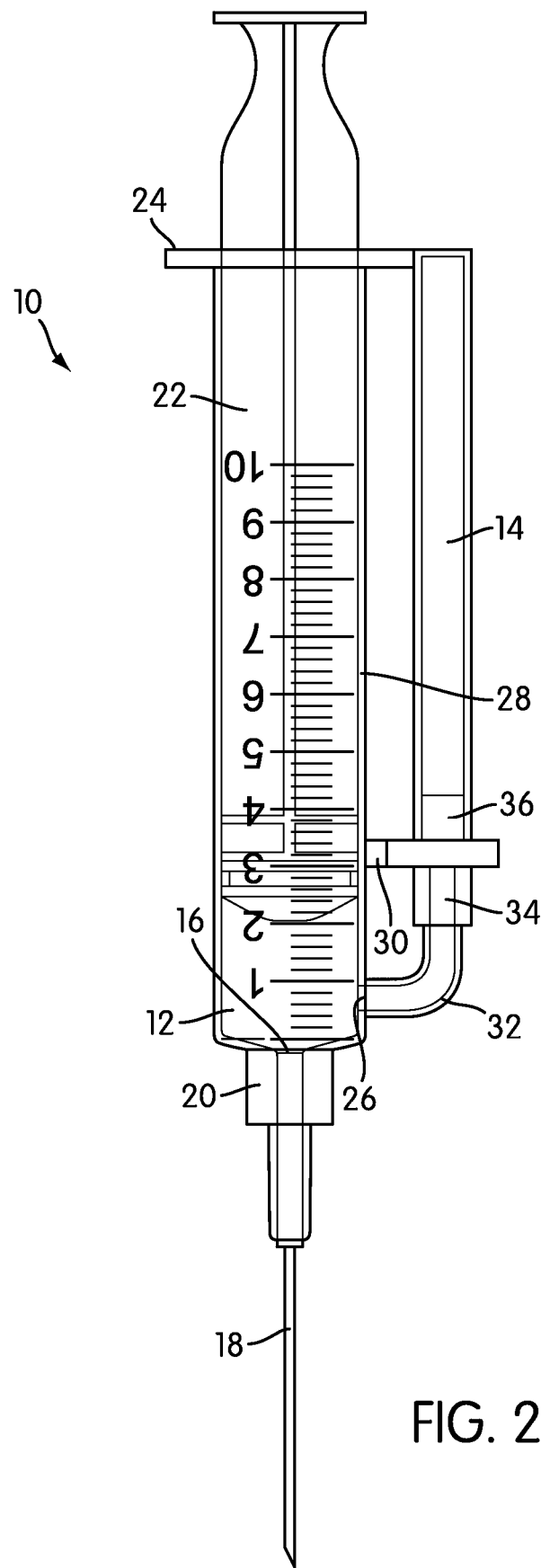
FIG. 2 is a front elevational view of the venous-arterial detector of FIG. 1.
Figure 3:
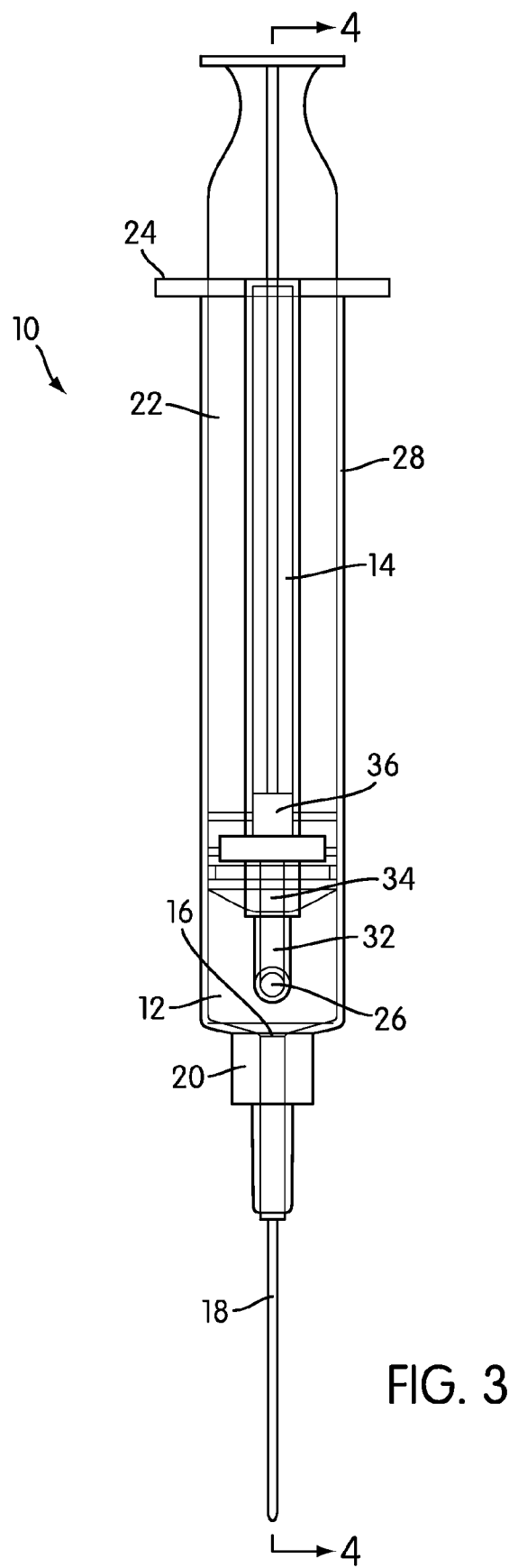
FIG. 3 is a side elevational view of the venous-arterial detector of FIG. 1.

FIG. 1 is a perspective view of a venous-arterial detector, generally indicated at 10, according to one embodiment of the invention. FIG. 2 is a front elevational view of the detector 10, and FIG. 3 is a side elevational view of the detector 10. The detector 10 has a primary or first chamber 12 and an indicator chamber 14.

The first chamber 12 has the general form of a syringe chamber; in the illustrated embodiment, it is generally cylindrical and has a first opening 16 at a first end. The first opening 16 places the first chamber 12 in fluid communication with a hollow needle 18, so that fluid flowing into the needle can flow into the first chamber 12. The needle 18 is physically connected to the first chamber 12 by appropriate connecting structure 20, which may differ from embodiment to embodiment. Generally speaking, it is advantageous if the connecting structure 20 allows the first chamber 12, and the detector 10 itself, to be detached from the needle 18.

The first chamber 12 also has a second end, which, in the illustrated embodiment, is closed and movably sealed by a plunger 22 that is constructed and arranged to draw fluid into the first chamber 12 through the needle 18 and to expel fluid from the first chamber 12 through the needle 18. An external flange 24 proximate to the second end of the first chamber 12 provides a surface against which to bear when a user is moving the plunger 22 along the first chamber 12. As indicated in the front elevational view of FIG. 2, the sidewall of the first chamber 12 may be graduated or otherwise marked so as to gauge the position of the plunger 22 along the first chamber 12 or for some other reason. Additionally, in some embodiments, the indicator chamber 14 may be graduated or otherwise marked.

The first chamber 12 also includes a second opening 26, which, in the illustrated embodiment, is formed in a lower portion of the sidewall 28 of the first chamber 12 proximate to the first opening 16 at the first end, although other placements of the second opening 26 may be used in other embodiments.

The second opening 26 places the first chamber 12 in fluid communication with the indicator chamber 14. In the illustrated embodiment, the first chamber 12 and the indicator chamber 14 are physically positioned side-by-side, and a supporting connector 30 attaches the two chambers 12, 14 near the first end of the first chamber 16. The indicator chamber 14 of the illustrated embodiment also attaches to the first chamber 12 at the flange 24.

The second opening 26 in the first chamber 12 opens to a short segment of tubing 32 that completes the fluid communication between the first chamber 12 and the indicator chamber 14. The tubing 32 may be somewhat flexible or substantially rigid, so long as it will not suffer adverse effects under moderate physiological pressures, as will be described below in greater detail.

Figure 4:
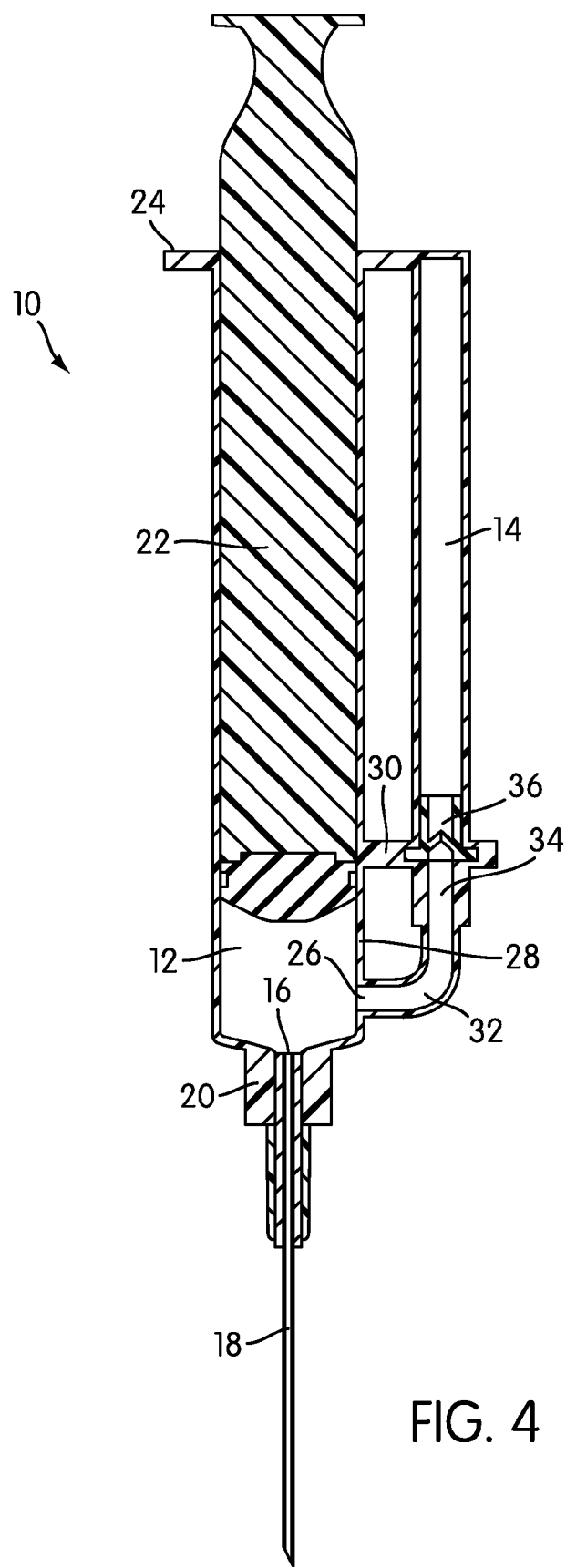
FIG. 4 is a cross-sectional view of the venous-arterial detector of FIG. 1, taken through Line 4-4 of FIG. 3.

FIG. 4 is a cross-sectional view of the detector 10, taken through Line 4-4 of FIG. 3. As can be seen in FIG. 4, the indicator chamber 14 has a single opening 34 into which the tubing 32 opens.

The indicator chamber 14 is pre-pressurized with a physiologically compatible fluid (i.e., gas or liquid) to a defined pressure. That defined pressure would generally be a pressure that is above the typical pressure found in a vein. In some embodiments, the defined pressure may be greater than an average mammalian venous blood pressure and less than an average mammalian arterial blood pressure. Pressures in the range of about 40 mm Hg to about 50 mm Hg above atmospheric pressure (about 800 mm Hg to about 810 mm Hg in absolute terms, presuming that the atmospheric pressure is 760 mm Hg) may be suitable for embodiments of the invention, and a pressure of at least 50 mm Hg may be particularly suitable, although the precise pressure that is used may vary from embodiment to embodiment and from patient to patient, as will be explained below.

The indicator chamber 14 is provided with a valve 36 that seals its opening 34 and places the indicator chamber 14 in selective fluid communication with the first chamber 12, so that the defined pressure within the indicator chamber 14 cannot pass through the valve 36 and thus remains within the indicator chamber, and fluid flowing from the first chamber 12 toward the indicator chamber 14 is permitted to pass through the valve 36. However, because of the defined pressure within the indicator chamber 14, any fluid that is to pass through the valve 36 and actually enter the chamber 14 would be of a higher pressure than the defined pressure.

As those of ordinary skill in the art will realize, the valve structure shown in the valve 36 in FIG. 4 is for illustrative purposes only. The precise type and structure of the valve 36 are not critical to the invention, so long as the valve 36 as a whole is constructed and arranged to prevent fluid from flowing out of the indicator chamber 14 and to allow fluid flowing into the indicator chamber 14 to pass through.

The indicator chamber 14 may be pressurized with the defined pressure in a number of ways, depending on the manner in which the detector 10 is made. For example, the indicator chamber 14 may be liquid or gas pressurized before it is mated with the first chamber 12 using water, air, nitrogen, carbon dioxide, or some other inert or physiologically-compatible fluid, or it may be pressurized after assembly by using the plunger 22 to create a negative pressure that draws fluid into the first chamber 12 and forces it into the indicator chamber 14. For example, if the indicator chamber 14 is to be pressurized after assembly, drawing a quantity of water into the first chamber 12 and then depressing the plunger 22 to drive some of that water through the second opening 26 and into the indicator chamber 14 has been found to be a suitable pressurization procedure. Graduations on the first chamber 12 and optionally, the indicator chamber 14, may be used to ensure that the correct amount of water or other fluid is placed in the indicator chamber 14.

Generally speaking, if the detector 10 is to be used on patients under sterile conditions, it is preferable if the detector 10 itself and the fluid used to pressurize it are sterile, although that need not be the case in all embodiments, particularly if the detector 10 is to be used in non-sterile environments. The precise manner in which the detector 10 is pressurized is not critical to the invention, so long as the indicator chamber 14 is pressurized with the defined pressure before the detector 10 is used.

Thus, the detector 10 operates because of the traditional pressure difference between artery and vein: since the indicator chamber 14 is pressurized to a defined pressure, blood will only be able to enter the indicator chamber 14 if that blood is at a pressure greater than the defined pressure in the indicator chamber 14. Therefore, if the defined pressure is set to a pressure higher than the typical venous pressure, if a vessel is punctured and no blood enters the indicator chamber 14, the vessel that was punctured is likely to be a vein, and if blood enters the indicator chamber 14, the punctured vessel is likely to be an artery.

This principle is illustrated in FIGS. 5A and 5B, which are cross-sectional views similar to FIG. 4. FIG. 5A illustrates the response of the detector to venipuncture. As shown, some blood may enter the first chamber 12, but the venous blood is at too low of a pressure for it to pass the valve 36 and enter the indicator chamber 14, and so none appears in the indicator chamber 14. FIG. 5B illustrates the response of the detector to arterial puncture. As shown, the arterial blood has a higher pressure than the defined pressure within the indicator chamber 14, and so some arterial blood passes through the valve and enters the indicator chamber 14. Simply put, in a typical situation, if the clinician sees blood in the indicator chamber 14, it is likely that he or she has punctured an artery.

As was noted above, different defined pressures may be used for different patients. For example, if a patient has an extremely high venous pressure, higher than the defined pressure, then blood will flow into the detector chamber upon venipuncture. In an opposite situation, if a patient is, for example, extremely hypovolemic and thus has an extremely low arterial pressure, lower than the defined pressure, arterial blood may not flow into the indicator chamber. Therefore, detectors 10 may be made with different defined pressures in some embodiments, in order to accommodate patients with extremely high venous pressure, extremely low arterial pressure, or other physiological conditions that would tend to affect whether arterial blood will flow into the indicator chamber 14.

In addition to differentiating between arteries and veins, the clinician also receives a simple indication of whether the pressure in the punctured vein is greater or less than the defined pressure within the indicator chamber 14. For that reason, the detector 10 may, in some embodiments, be used as a pressure indicator.

The precise manner in which the detector 10 is used may be left to the discretion of the clinician. In some embodiments, after puncturing a vessel, the clinician may draw back on the plunger 22 in order to lower the pressure in the first chamber 12 and aspirate blood into the first chamber 12. However, in some clinical situations, aspiration of blood may not be necessary or desirable.

If the detector 10 is to be used with aspiration, then the defined pressure within the indicator chamber 14 may be altered to take into account the negative pressure within the first chamber 12 if necessary or desired, and clinicians may be taught to aspirate or draw back the plunger 22 in a calibrated fashion. For example, a clinician may be instructed to draw the plunger 22 up only to a certain graduated mark on the first chamber 12.

Alternatively, if the indicator chamber 14 is pre-pressurized during manufacture and the plunger 22 is not needed to pressurize the indicator chamber 14 or to aspirate, embodiments of the invention may be made without a plunger 22.

Once the detector 10 has served its purpose and determined whether a punctured vessel is an artery or a vein, the needle 18 and its connecting structure 20 may be disconnected from the rest of the detector 10 so that they can remain in place in the vessel. Preferably, the connecting structure 20 has a standard type of connection so that other devices and instruments can then be connected to the properly placed needle 18. For example, in a central line insertion where the clinician is attempting to locate the internal jugular vein, once venipuncture is performed, the detector 10 may be removed and a central line catheter inserted over or through the needle 18, per the typical procedure.

The gauge of the needle 18 is not critical to the invention so long as blood can flow through it relatively freely. In at least some embodiments, an 18-gauge needle 18 may be used.

FIGS. 1-5 illustrate a single embodiment of the invention in which the first chamber 12 and the indicator chamber 14 are physically separate and fixedly connected to one another. However, other embodiments may employ different configurations of the two chambers 12, 14 and the other components.

Figure 6:
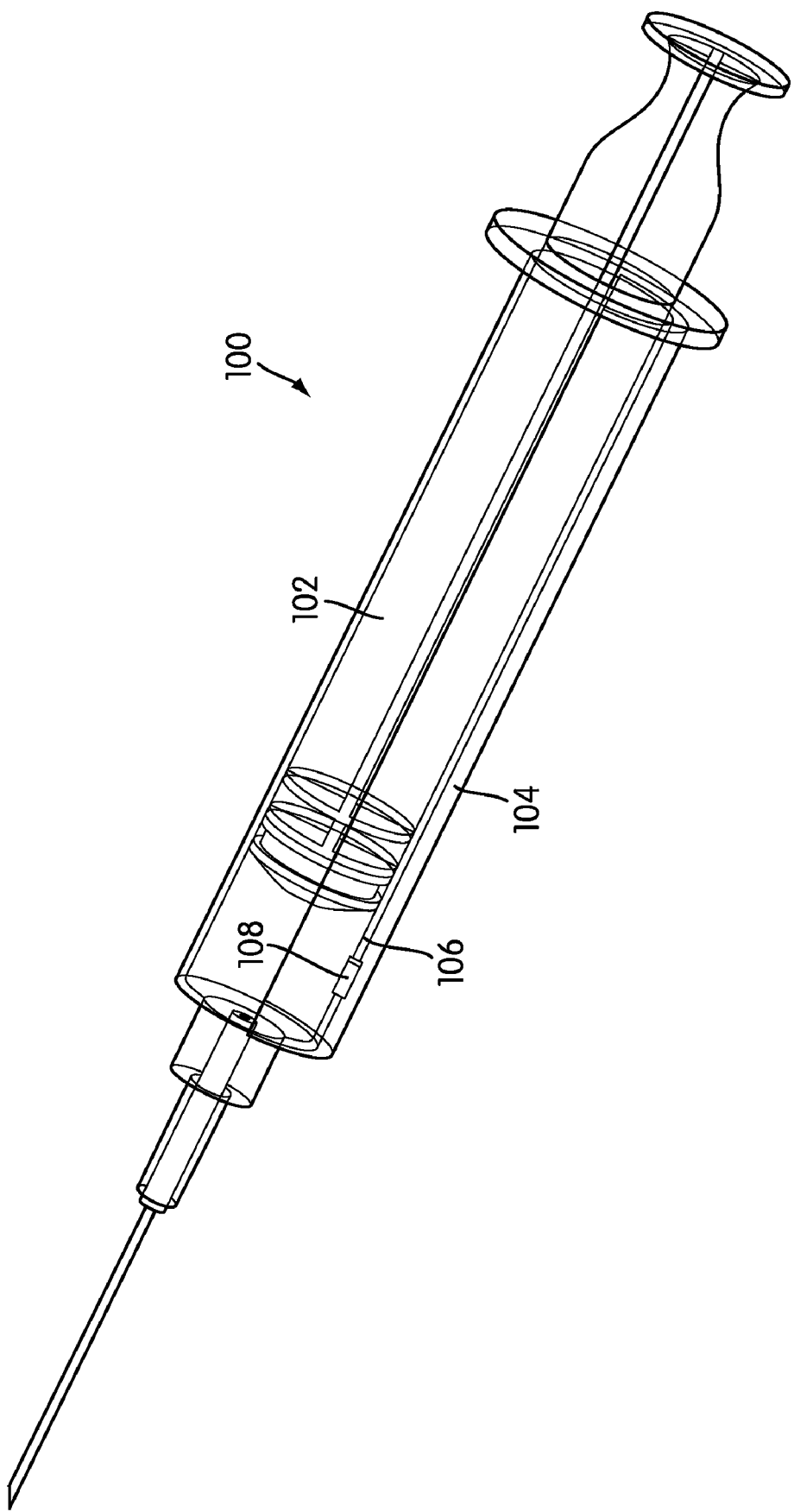
FIG. 6 is a perspective view of a venous-arterial detector according to another embodiment of the invention.

As one example, FIG. 6 is a perspective view of another embodiment of a venous-arterial detector, generally indicated at 100. The principle of operation of the detector 10 and the detector 100 is the same and, unless otherwise indicated, the components of the detector 100 may be assumed to be similar to those of the detector 10.

The detector 100 has a first chamber 102 that is generally cylindrical and an indicator chamber 104 that is relatively flattened and curves around at least a portion of the exterior of the first chamber 104, giving the detector 100 as a whole a generally cylindrical, although slightly eccentric, shape. The two chambers 102, 104 share a sidewall 106, and a valve 108 is positioned in an opening in that sidewall 106.

In some embodiments, the indicator chamber 104 may wrap entirely around the first chamber 102, so that the indicator chamber 104 has the form of a cylindrical ring or hollow cylinder. However, one advantage of the detector 100 as illustrated in FIG. 5 is that the diameter of the detector 100 is not increased over its entire circumference. Whichever variation is employed, the shape of a detector like the detector 100 may make it easier to grip and use.

Figure 7:
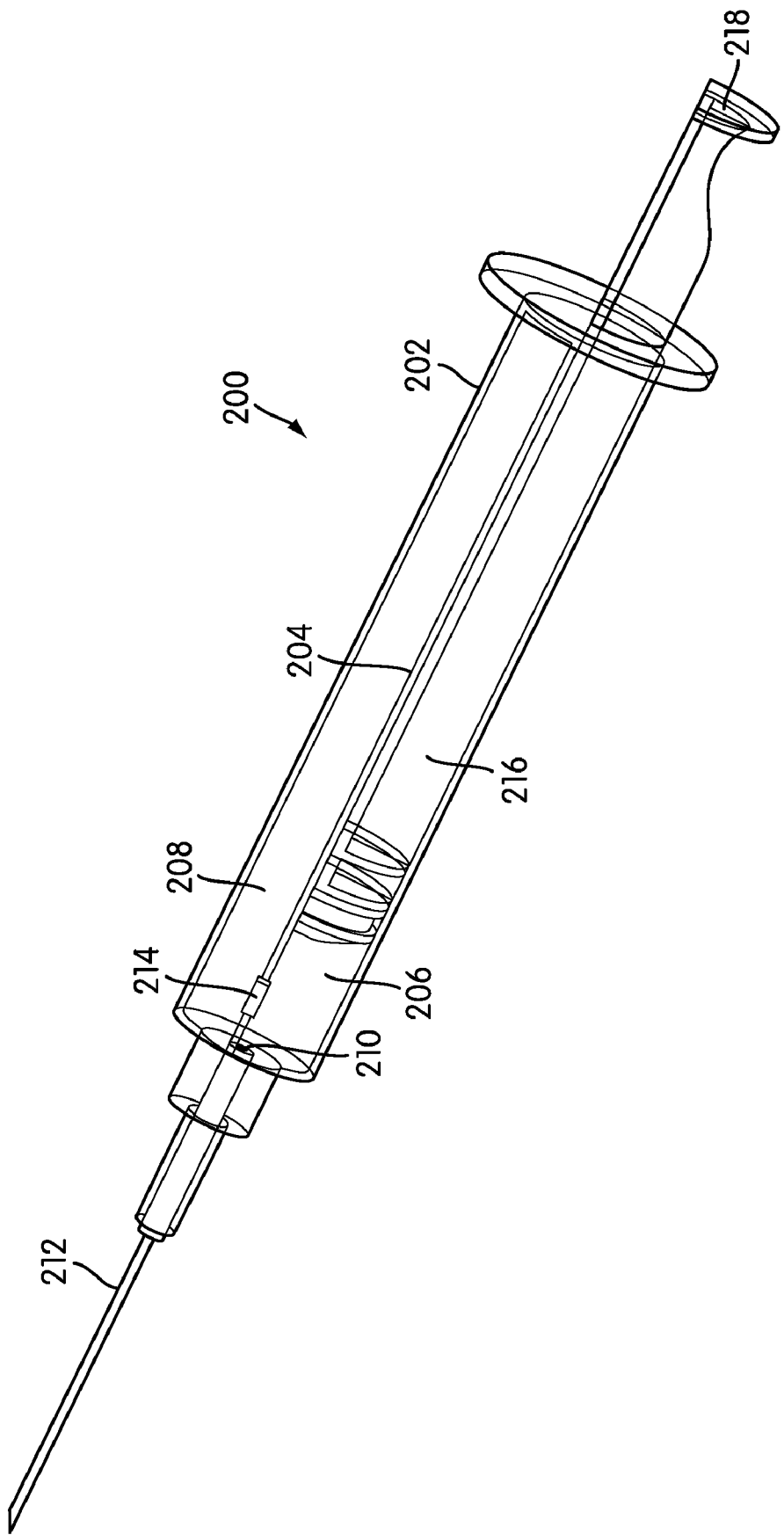
FIG. 7 is a perspective view of a venous-arterial detector according to yet another embodiment of the invention.

FIG. 7 is a perspective view of another embodiment of a venous-arterial detector, generally indicated at 200. The principle of operation of the detectors 10, 100 and the detector 200 is the same and, unless otherwise indicated, the components of the detector 200 may be assumed to be similar to those of the detectors 10, 100 of the other embodiments.

The detector 200 has a body 202 with the generally cylindrical shape of a typical syringe. The body 202 of the detector 200 is split longitudinally by a wall 204 that divides the body 202 into a first chamber 206 and an indicator chamber 208. The wall 204 does not extend along the longitudinal centerline of the body 202; instead, it is slightly offset to one side, so that the first opening 210 that communicates with the needle 212 is entirely within the first chamber 206. A plunger 216 is mounted within and movably seals the first chamber 206; however, the plunger 216 is longitudinally sectioned and shaped to fit within the first chamber 206.

A valve 214 provided in an opening in the wall 204 places the first chamber 206 in fluid communication with the indicator chamber 208 and acts as do the valves 36, 108 of the other embodiments 10, 100.

Although the wall 204 that divides the two chambers 206, 208 in the detector 200 is slightly offset from the longitudinal centerline of the detector 200, the wall 204 may be placed in essentially any convenient position within the body 202 of the detector 200, so long as the first opening 210 opens to the first chamber 206. In some embodiments, the volume of the indicator chamber 208 may be substantially less than that of the first chamber 208. Moreover, as those of skill in the art will realize, the volume of the indicator chambers 14, 104, 208 in embodiments of the present invention is generally not critical so long as the indicator chamber 14, 104, 208 has an appropriate volume to hold an amount of blood sufficient to be seen for indicative purposes.

Additionally, although the end 218 of the plunger 216 is shown in FIG. 7 as being longitudinally sectioned, the end of the plunger may be fully circular or have any other shape desirable in allowing a user to actuate it.

Embodiments of the detector 10, 100, 200 may be made from plastic, glass, or any other suitable material. In some embodiments, it may be most advantageous to make detectors 10, 100, 200 from plastic.

As those of skill in the art will appreciate, one advantage of the detector 10 is that it can be made by slightly modifying existing syringes; for example, the first chamber 12 and associated structures may be a modified conventional syringe, and the indicator chamber 14 may comprise the body of a smaller syringe, modified to include the valve 36. Embodiments of the detector 100, 200 in which the first and second chambers are integral would generally be made by molding, such as injection molding.

Although the invention has been described with respect to certain embodiments, those embodiments are intended to be exemplary, rather than limiting. Modifications and changes may be made within the scope of the claims.

What is claimed is:

1. A venous-arterial detector, comprising:
   a first chamber having first opening at a first end and a second opening in a wall thereof;
   a needle connected to and in fluid communication with the first chamber through the first opening;
   an indicator chamber pressurized before use to a defined pressure that is greater than a venous blood pressure and less than an arterial blood pressure, the indicator chamber being connected to the first chamber through the second opening in the first chamber, the first chamber and the indicator chamber being fixedly attached to one another; and a valve interposed between the first chamber and the indicator chamber so as to place the indicator chamber in selective fluid communication with the first chamber, the valve being constructed and arranged such that (1) the defined pressure within the indicator chamber cannot pass through the valve, and thus remains within the indicator chamber, and (2) fluid flowing from the first chamber toward the indicator chamber is permitted to pass through the valve;

wherein blood entering the first chamber through the needle flows into the indicator chamber if the pressure of the entering blood is greater than the defined pressure within the indicator chamber.

2. The venous-arterial detector of claim 1, further comprising a plunger movably sealing the first chamber, the plunger being constructed and arranged to draw fluid into the first chamber through the needle and to drive fluid out of the first chamber through the needle.

3. The venous-arterial detector of claim 1, wherein the first chamber is generally cylindrical.

4. The venous-arterial detector of claim 3, wherein the indicator chamber is generally cylindrical.

5. The venous-arterial detector of claim 4, wherein the first chamber and the indicator chamber are arranged side-by-side and are connected by a short segment of tubing.

6. The venous-arterial detector of claim 1, wherein the indicator chamber extends circumferentially around at least a portion of the first chamber.

7. The venous-arterial detector of claim 1, wherein the second opening is proximate to the first end.

8. The venous-arterial detector of claim 1, wherein the defined pressure is a pressure in the range of from about 40 mm Hg to about 50 mm Hg above ambient atmospheric pressure.

9. The venous-arterial detector of claim 1, wherein the defined pressure is at least 50 mm Hg above ambient atmospheric pressure.

10. The venous-arterial detector of claim 1, wherein the needle is disconnectable from the venous-arterial detector.

11. The venous-arterial detector of claim 1, wherein the venous-arterial detector comprises a generally cylindrical body that is divided generally longitudinally by a wall to define the first chamber and the indicator chamber.

12. The venous-arterial detector of claim 11, wherein the valve is disposed in the wall dividing the body.

13. The venous-arterial detector of claim 11, further comprising a plunger movably sealing the first chamber, the plunger being constructed and arranged to draw fluid into the first chamber through the needle and to drive fluid out of the first chamber through the needle.

14. The venous-arterial detector of claim 6, wherein the valve is disposed in a wall separating the first chamber from the indicator chamber.

15. A venous-arterial detector, comprising:

a body having a sidewall and a bottom, the body being divided generally longitudinally by a wall so as to define a first chamber and an indicator chamber within the body, the wall having a first opening therein, thereby placing the first chamber and the indicator chamber in fluid communication with one another, the bottom of the body defining a second opening located within the first chamber, and the indicator chamber being pressurized before use to a defined pressure that is greater than a venous blood pressure and less than an arterial blood pressure;

a needle connected to and in fluid communication with the first chamber through the second opening; and a valve disposed in the first opening of the wall so as to be interposed between the first chamber and the indicator chamber, thereby placing the indicator chamber in selective fluid communication with the first chamber, the valve being constructed and arranged such that (1) the defined pressure within the indicator chamber cannot pass through the valve, and thus remains within the indicator chamber, and (2) fluid flowing from the first chamber toward the indicator chamber is permitted to pass through the valve;

wherein blood entering the first chamber through the needle flows into the indicator chamber if the pressure of the entering blood is greater than the defined pressure within the indicator chamber.

16. The venous-arterial detector of claim 15, wherein the needle is disconnectable from the venous-arterial detector.

17. The venous-arterial detector of claim 15, further comprising a plunger movably sealing the first chamber, the plunger being constructed and arranged to draw fluid into the first chamber through the needle and to drive fluid out of the first chamber through the needle.

18. The venous-arterial detector of claim 17, wherein the body further comprises a top that seals the indicator chamber.

19. A venous-arterial detector, comprising:

a first chamber having first opening at a first end and a second opening in a wall thereof;

a needle connected to and in fluid communication with the first chamber through the first opening;

a plunger movably sealing the first chamber, the plunger being constructed and arranged to draw fluid into the first chamber through the needle and to drive fluid out of the first chamber through the needle;

an indicator chamber pressurized before use to a defined pressure that is greater than a venous blood pressure and less than an arterial blood pressure, the indicator chamber being connected to the first chamber through the second opening in the first chamber, the first chamber and the indicator chamber being fixedly attached to one another; and a valve interposed between the first chamber and the indicator chamber so as to place the indicator chamber in selective fluid communication with the first chamber, the valve being constructed and arranged such that (1) the defined pressure within the indicator chamber cannot pass through the valve, and thus remains within the indicator chamber, and (2) fluid flowing from the first chamber toward the indicator chamber is permitted to pass through the valve;

wherein blood entering the first chamber through the needle flows into the indicator chamber if the pressure of the entering blood is greater than the defined pressure within the indicator chamber.

20. The venous-arterial detector of claim 19, wherein the needle is disconnectable from the venous-arterial detector.

* * * * *